United States Patent [19]
Russo

[11] Patent Number: 4,944,732
[45] Date of Patent: Jul. 31, 1990

[54] GASTROSTOMY FEEDING PORT

[75] Inventor: Ronald D. Russo, Barrington, R.I.

[73] Assignee: Sandoz Nutrition Corporation, Minneapolis, Minn.

[21] Appl. No.: 232,597

[22] Filed: Aug. 15, 1988

[51] Int. Cl.⁵ .............................................. A61M 39/02
[52] U.S. Cl. .................................... 604/247; 604/105; 604/175; 604/256
[58] Field of Search ............... 604/264, 174, 175, 178, 604/247, 256, 93, 104, 105

[56] References Cited

U.S. PATENT DOCUMENTS

| | | | |
|---|---|---|---|
| 4,393,873 | 7/1983 | Nawash et al. | 604/174 |
| 4,666,433 | 5/1987 | Parks | 128/DIG. 26 |
| 4,776,848 | 10/1988 | Solazzo | 604/247 |
| 4,863,438 | 9/1989 | Gauderer | 604/247 |

*Primary Examiner*—Stephen C. Pellegrino
*Attorney, Agent, or Firm*—Salter & Michaelson

[57] ABSTRACT

A gastrostomy feeding port includes a deformable, conical tip portion having at least one side aperture therethrough, a tube portion which extends rearwardly from the tip portion, a fitting portion on the rear end of the tube portion, a removable valve portion in the fitting portion and a flange portion which extends outwardly from the fitting portion. The feeding port is adapted to be installed in a patient so that the tube portion extends through a preestablished stoma in the patient's stomach with the tip portion located in the patient's stomach and the fitting portion and the flange portion engaging the skin of the patient adjacent the stoma. Since the valve portion is removable received in the fitting portion, it can be repaired or replaced if needed without replacing the entire feeding port.

16 Claims, 3 Drawing Sheets

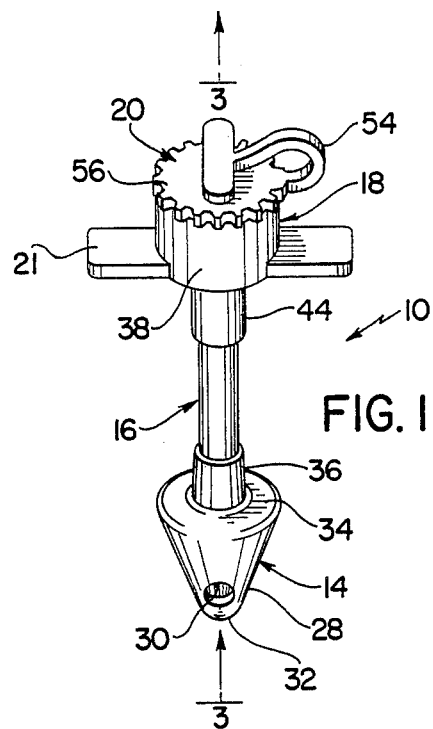
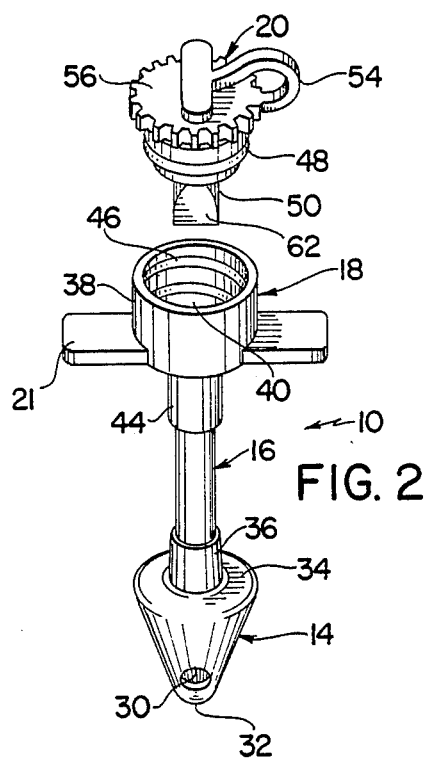
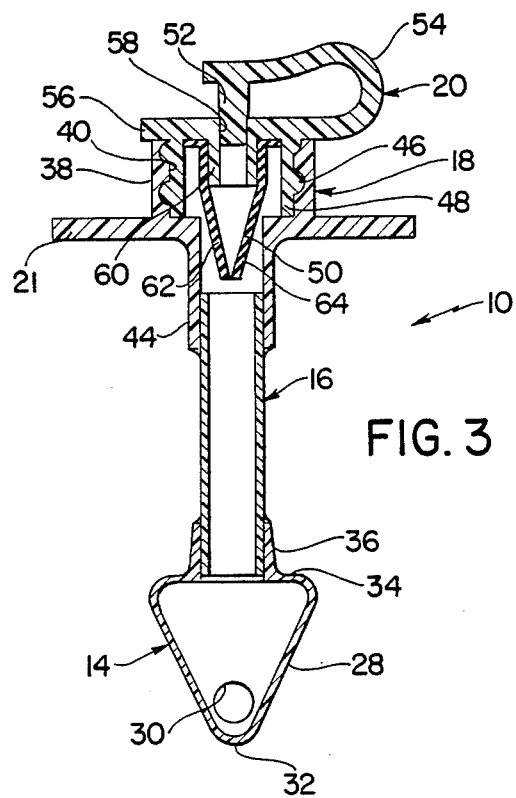

GASTROSTOMY FEEDING PORT

BACKGROUND AND SUMMARY OF THE INVENTION

The instant invention relates to medical apparatus and more particularly to a gastrostomy port for feeding a patient over a prolonged period of time through a previously established stoma in the patient's stomach.

It is widely recognized that gastrostomy stomas can be effectively utilized over prolonged periods of time for feeding and medicating certain types of patients, such as those having swallowing difficulties. In this regard, various catheter assemblies including those comprising de Pezzer catheters and Foley catheters, have been widely used for administering feeding formulas through gastrostomy stomas in the stomachs of patients. However, most of the heretofore available feeding catheter assemblies have severely restricted patient mobility, and therefore gastrostomy patient's wearing these devices have generally not been able to participate in many types of physical activities. Further, since most of the heretofore available gastrostomy catheter assemblies have been relatively obtrusive and cosmetically displeasing; they have often been a source of embarassment and phychological trauma.

In addition to de Pezzer and Foley catheter assemblies, a recently developed device known as the Gastrostomy Button (American Endoscopy Inc. TM) has been utilized for feeding gastrostomy patients through preestablished stomas. This device, which represents the closest prior art to the subject invention of which the applicant is aware comprises a tip portion which resembles the tip of a de Pezzer cathether, a rubber flap-type check valve in the tip portion, a tube portion which extends rearwardly from the tip portion and a rear flange on the rear end of the tube portion. The Gastrostomy Button device is adapted to be installed in a preestablished stoma in a patient so that the tip portion is positioned against the inner stomach wall and so that the flange portion engages the skin of the patient adjacent the stoma. However, although it has been found that the Gastrostomy Button has advantages over some of the other types of heretofore available devices of this general type due to its relatively small size, it has been found that the check valve in this device has a tendency to become easily clogged due to encrustation and that it can also become damaged or dislodged during obturation so that it is incapable of preventing reflux. Further, due to the overall construction of this device, it must generally be replaced if a malfunction in the check valve occurs.

The instant invention provides an improved gastrostomy feeding port which has significant advantages over virtually all of the heretofore available gastrostomy feeding devices. Specifically, the instant invention provides a relatively small, unobtrusive gastrostomy feeding port which is operative with a substantially increased level of reliability and effectiveness compared to the heretofore available gastrostomy feeding devices. The device of the subject invention comprises a tip portion which is made of a deformable rubberized material in a substantially hollow conical configuration, and has at least one side aperture therein. The device further comprises a tube portion which extends rearwardly from the tip portion, a fitting portion on the rear end of the tube portion, and a valve portion which is received in the fitting portion. The tube portion is dimensioned to pass through a preestablished gastrostomy stoma in a patient and the fitting portion is adapted to be connected to a tubular fitting for connecting the feeding port to a supply of feeding formula. The valve portion is removably received in the fitting portion and it is operative for permitting the flow of a fluid, such as a feeding formula into the stomach of a patient and for preventing the reverse flow of fluid back through the feeding port. The valve portion preferably comprises a duck-bill type valve and it is preferably threadedly received in an interior cavity in the fitting portion. In addition, the gastrostomy feeding port preferably further comprises a concave resilient flange on the fitting portion which faces towards the tip portion, and is engageable with the skin of a patient adjacent a stoma for biasing the tip portion against the inner wall of the patient's stomach.

It has been found that the gastrostomy feeding port of the instant invention has certain specific advantages over the hertofore available gastrostomy feeding devices. Specifically, it has been found that because the valve portion is removably received in the fitting portion, it can be removed during obturation, and thereafter installed in the fitting portion so that it effectively prevents reflux of fluids from the stomach of the patient. Further, since the valve preferably comprises a duckbill type valve, it is not proned to becoming inadvertently dislodged and since it is removably received in the fitting portion, it can be replaced without replacing the entire feeding port. It can also be removed in the event that draining or decompression of the patient's stomach becomes necessary. Still further, because the feeding port includes a concave flange portion on the fitting portion, the feeding port is operative for biasing the tip portion against the inner wall of a patient's stomach so that a more effective and complete seal is achieved between the tip portion and the inner wall of the stomach.

Accordingly, it is a primary object of the instant invention to provide an improved gastrostomy feeding port.

Another object of the instant invention is to provide a gastrostomy feeding port having a removable antireflux valve.

Another object of the instant invention is to provide a gastrostomy feeding port having means for biasing the tip portion thereof against the inner wall of a patient's stomach in order to achieve an improved seal between the feeding port and the stomach wall.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a perspective view of the gastrostomy feeding port of the instant invention;

FIG. 2 is an exploded perspective view thereof;

FIG. 3 is an enlarged sectional view taken along line 3—3 in FIG. 1;

DESCRIPTION OF THE INVENTION

Figure 4:
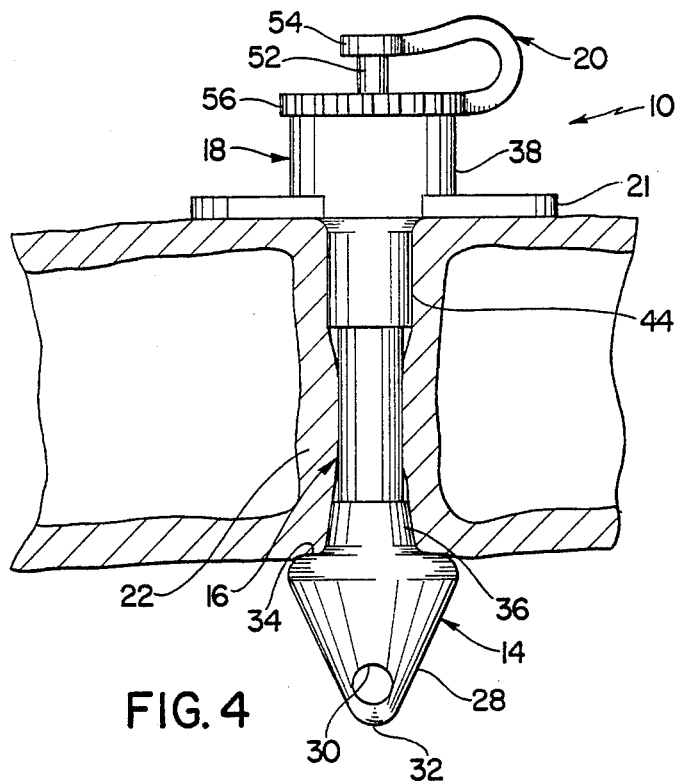
FIG. 4 is an enlarged sectional view of the feeding port installed in a stoma in the stomach of a patient.
Figure 5:
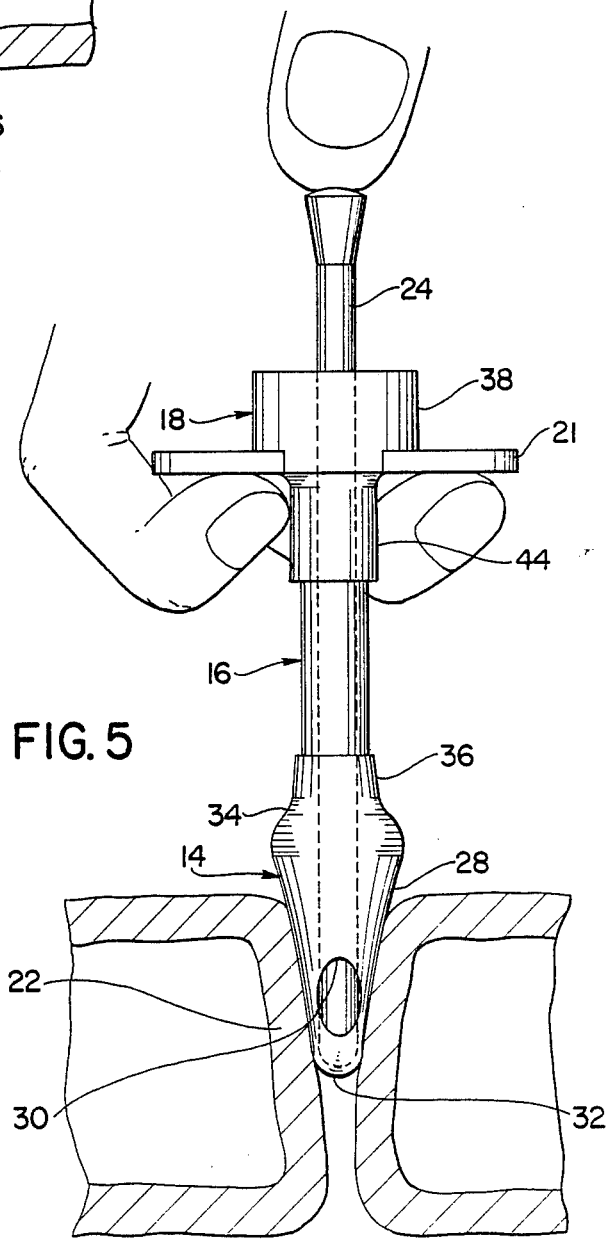
FIG. 5 is a similar view illustrating the obturation of the feeding port with the valve portion removed.
Figures 6, 7:
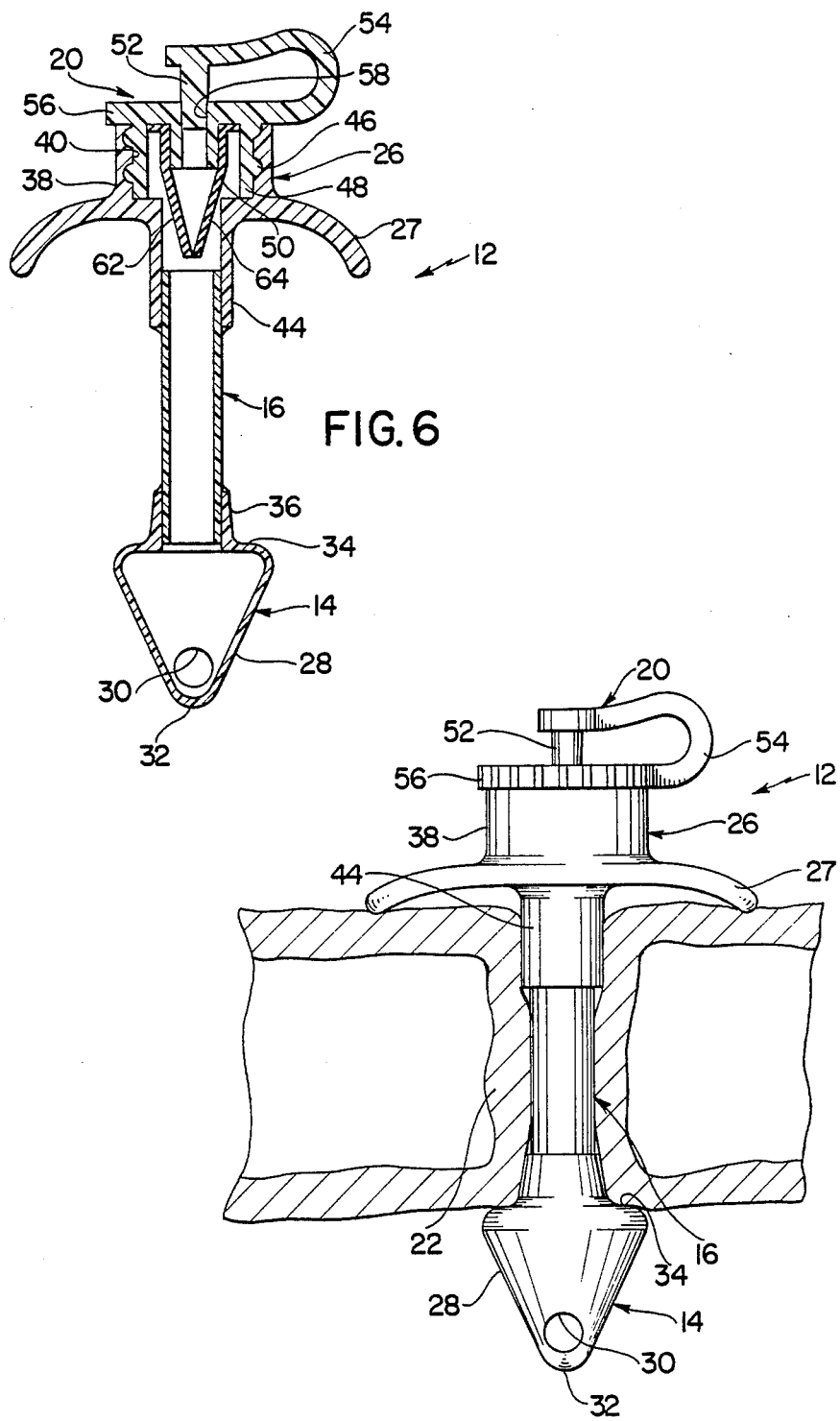
FIG. 6 is an enlarged sectional view of a second embodiment of the feeding port.
FIG. 7 is an enlarged sectional view illustrating the feeding port installed in a stoma in the stomach of a patient.

Referring now to the drawings, a first embodiment of the gastrostomy feeding port of the instant invention is illustrated and generally indicated at 10 in FIGS. 1-4, and a second embodiment of the feeding port is illustrated and generally indicated at 12 in FIGS. 6 and 7. The feeding port 10 comprises a tip portion generally indicated at 14, a tube portion generally indicated at 16, a fitting portion generally indicated at 18, a valve portion generally indicated at 20 and a flange portion 21. The feeding port 10 is adapted to be installed in a stoma 22 in the stomach of a patient utilizing an obturator 24 in the manner illustrated in FIG. 5 so that the feeding port 10 is positioned in the fully installed position illustrated in FIG. 4. The feeding port 12 comprises a tip portion 14, a tube portion 16 a valve portion 20, a fitting portion 26, and a flange portion 27 and it is adapted to be installed in a stoma 22 so that it is positioned in the manner illustrated in FIG. 7.

Referring first to the feeding port 10, the tip portion 14 thereof is of generally hollow conical configuration, and it includes a substantially straight sidewall 28 having a pair of side apertures 30 therethrough, a rounded terminal end portion 32, an inwardly extending rear wall 34, and a tubular sleeve 36 which communicates with the interior of the tip portion 14 and extends rearwardly from the rear wall 34. The tip portion 14 is preferably integrally formed from a resiliently deformably biocompatible plastic material, such as a silicon rubber.

The tubular portion 16 preferably comprises a hollow tube which is made of a resiliently deformable biocompatible plastic material, such as silicon rubber. The tube portion 16 is received in the sleeve 36, and permanently secured to the tip portion 14 with a suitable adhesive, such as a silicon rubber adhesive, so that it provides a clear, unobstructed passageway into the tip portion 14.

The fitting portion 18 is illustrated most clearly in FIG. 3 and it comprises a relatively short, cylindrical housing section 38 having an interior cavity 40 therein, and a tubular sleeve 44 which extends forwardly from the housing section 38 to define a tubular passage which commuicates with the cavity 40. Inner screw threads 46 are formed in the housing section 38 to enable the valve portion 20 to be received in threaded engagement therein. The housing section 38, and the sleeve 44 are preferably all integrally formed from a suitable deformable, biocompatible plastic material, such as a silicon rubber, and the tubular portion 16 is received and secured in the sleeve 44 with a suitable adhesive, such as a silicone adhesive.

The valve portion 20 comprises a threaded plug 48, a valve element 50, a stopper 52 and a flexible arm 54, which attaches the stopper arm 52 to the plug 48. The plug 48 is adapted to be received in threaded engagement in the interior cavity 40, and it includes a cap 56 having an aperture 58 therethrough and a tubular neck 60 which communicates with the aperture 58 and extends inwardly into the cavity 40 from the cap 56. The aperture 58 is adapted to receive a male Leur connector for connecting the feeding portion to a feeding formula supply tube. The stopper 52 is receivable in engagement in the aperture 58, and the plug portion 48, the stopper 52 and the flexible arm 54 are preferably all integrally formed from a suitable, biocompatible plastic material such as a semirigid PVC. The valve element 50 comprises a duck-bill type valve element having converging sides 62 and 64 which are resiliently separable to permit the passage of a fluid therethrough in one direction but not in the reverse direction. The base portion of the valve element 50 is received in a resiliently expanded disposition on the tubular neck 60 to secure the valve element 50 to the plug 48. The valve portion 20 is constructed so that when the plug 48 is received in threaded engagement in the fitting portion 18, the valve element 50 is received in the cavity 40 and extends partially into the tubular sleeve 44, although the valve element 50 is preferably spaced inwardly at least slightly from the inner side of the tubular sleeve 44 as illustrated in FIG. 3.

The flange 21 is preferably integrally formed with the housing section 38 and it comprises a pair of leaves which extend outwardly from opposite sides of the housing section 38 to prevent the fitting portion 18 from being drawn inwardly into the stomach of a patient.

Referring now to FIG. 5, the preferred manner for installing the feeding port 10 in a stoma 22 in the stomach of a patient is illustrated. In this connection, prior to installing the feeding port 10, the valve portion 20 is preferably removed from the fitting portion 18, and the obturator 24 is inserted into the feeding port 10 so that it passes into the tip portion 14. The obturator 24 preferably comprises an elongated rod having a rounded or blunt end, and it is inserted into the feeding port 10 so that the blunt end thereof is received in the tip portion 14. Thereafter, by urging the obturator 24 forwardly, the tip portion 14 can be deformed to an elongated configuration so that it can be more easily passed through the stoma 22. In this regard, various lubricants, including those containing local anesthetics, can be preapplied to the tip portion 4 in accordance with know medical practice in order to facilitate the installation of the feeding port 10 in the stoma 22. In any event, once the tip portion 14 has been passed through the stoma 22, the obturator 24 can be removed, and the valve portion 20 can be assembled in the fitting portion 18. The feeding port 10 is preferably dimensioned so that the distance between the rear wall 34 and the flange portion 21 is approximately equal to the stoma depth so that the rear wall 34 engages the inner wall of the stomach and the flange portion 21 engages the outer surface of the skin of the patient adjacent the stoma 22. After the feeding port 10 has been installed in a patient in this manner, the stopper 52 can be removed from the aperture 58, and a feeding formula supply tube can be connected to the plug 48 in order to supply feeding formula to the patient. In the event that the valve element 50 becomes clogged or malfunctions, the valve portion 20 can be unscrewed from the fitting portion 18, and a new valve portion 20 can be installed without removing the entire feeding port 12 from the patient.

Referring now to FIGS. 6 and 7, the feeding port 12 comprises a tip portion 14, a tubular portion 16, a fitting portion 18, a valve portion 20 and a flange portion 27. The tip portion 14, the tubular portion 16, the fitting portion 18 and the valve portion 20 are preferably identical to their corresponding elements in the feeding port 10. However, the flange portion 27 is curved instead of substantially straight like the flange portion 21. In this regard, the flange portion 21 comprises a pair of outwardly extending leaves which curve toward the tip portion 14, and it is preferably integrally molded with the fitting portion 18 from a suitable, resiliently deformable, plastic material, such as a silicon rubber. The flange portion 27 is resiliently deformable to a somewhat more straightened disposition as illustrated in FIG. 7. Accordingly, when the feeding port 12 is properly dimensioned for an appropriate stoma depth, the flange portion 21 can be effectively utilized for biasing the rear wall 34 of the tip portion 14 against the inner wall of the stomach adjacent the stoma 22 to achieve a more positive seal between the tip portion 14 and the inner wall of the stomach.

The feeding port 12 is adapted to be installed in a patient in a manner similar to that hereinabove described with respect to the feeding port 10 utilizing an obturator 24. Thereafter, the feeding port 12 can be effectively utilized for administering feeding formula to the patient over a prolonged period of time, and the valve portion 20 of the feeding port 12 can be replaced if needed without replacing the remaining components of the feeding port 12.

It is seen therefore that the instant invention provides an effective gastrostomy feeding port which has specific advantages over the heretofore available feeding ports. In this connection, the valve portions 20 of the feeding ports 10 and 12 are located in their respective fitting portions so that they can be removed during obturation and replaced, cleaned or repaired if needed. Further, the valve elements 50 effectively prevent backflow of fluids or gases; although, the valve portions 20 can be easily removed to permit decompression or fluid drainage. Hence, for these reasons as well as the other reasons hereinabove set forth, it is seen that the instant invention represents a significant advancement in the art which has substantial commercial significance.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A gastrostomy feeding port comprising a tip portion, a tube portion, a fitting portion and a valve portion, said tip portion being receivable through a preestablished stoma in the stomach of a patient and being operative for passing a fluid into said stomach, said tip portion including retaining means engageable with the inner wall of said stomach for preventing the inadvertent removal of said feeding port from said stoma, said tube portion communicating with said tip portion for passing said fluid thereto and extending rearwardly therefrom, said tube portion being dimensioned to extend outwardly through said stoma when said tip portion is in engagement with the inner wall of the stomach of said patient, said fitting portion being of a low-profile configuration and being attached to the rear end of said tube portion so that said fitting portion is disposed substantially on the exterior of said patient adjacent the skin surrounding said stoma when said tip portion is in engagement with said inner stomach wall, said valve portion being disposed substantially in said fitting portion and being accessible from the exterior of said patient, said valve portion comprising a valve element which is operative for permitting the flow of a feeding formula into said tube portion from said fitting portion and for preventing the reverse flow of said feeding formula and a closure element which is operative for removably sealing said fitting portion without interferring with said valve element.

2. In the gastrostomy feeding port of claim 1, said tip portion being of hollow conical configuration and being deformable to pass said tip portion through said stoma.

3. In the gastrostomy feeding port of claim 1, said valve portion being threadedly received in said fitting portion.

4. In the gastrostomy feeding port of claim 1, said valve portion comprising duck-bill type valve.

5. The gastrostomy feeding port of claim 1 further comprising means biasing on said tip portion biasing the latter against the inner side of the stomach wall of said patient.

6. In the gastrostomy feeding port of claim 5, said biasing means comprising an outwardly extending concave flange on said fitting portion facing toward said tip portion, said flange being resiliently deformable and being engageable with the skin of said patient adjacent said stoma for biasing said tip portion against the inner wall of the patient's stomach.

7. In the gastrostomy feeding port of claim 1, said valve portion being removably received in said fitting portion.

8. A gastrostomy feeding port comprising a tip portion, a tube portion, a fitting portion and a valve portion, said tip portion being receivable through a preestablished stoma in the stomach of a patient and being operative for passing a fluid into said stomach, said tip portion including retaining means engageable with the inner wall of said stomach for preventing the inadvertent removal of said feeding port from said stoma, said tube portion communicating with said tip portion for passing said fluid thereto and extending rearwardly therefrom, said tube portion being dimensioned to extend outwardly through said stoma when said tip portion is in engagement with the inner wall of the stomach of said patient, said fitting portion being of a low-profile configuration and being attached to the rear end of said tube portion so that said fitting portion is disposed substantially on the exterior of said patient adjacent the skin surrounding said stoma when said tip portion is in engagement with said inner stomach wall, said valve portion being removably received in said fitting portion and being accessible from the exterior of said patient, said valve portion being operative for permitting the flow of a feeding formula into said tube portion from said fitting portion and for preventing the reverse flow of said feeding formula.

9. In the gastrostomy feeding port of claim 8, said tip portion being of hollow conical configuration and being deformable to pass said tip portion through said stoma.

10. In the gastrostomy feeding port of claim 8, said valve portion being threadedly received in said fitting portion.

11. In the gastrostomy feeding port of claim 8, said valve portion comprising a duck-bill type valve.

12. The gastrostomy feeding port of claim 8 further comprising means biasing on said tip portion biasing the latter against the inner side of the stomach wall of said patient.

13. In the gastrostomy feeding port of claim 12, said biasing means comprising an outwardly extending concave flange on said fitting portion facing toward said tip portion, said flange being resiliently deformable and being engageable with the skin of said patient adjacent the stoma for biasing said tip portion against the tinner wall of the patient's stomach.

14. A gastrostomy feeding port comprising a tip portion, a tube portion, a fitting portion and a valve portion, said tip portion being receivable through a preestablished stoma in the stomach of a patient and being operative for passing a fluid into said stomach, said tip portion including retaining means engageable with the inner wall of said stomach for preventing the inadvertent removal of said feeding port from said stoma, said tub portion communicating with said tip portion for passing said fluid thereto and extending rearwardly therefrom, said tube portion being dimensioned to extend outwardly through said stoma when said tip portion is in engagement with the inner wall of the stomach of said patient, said fitting portion being attached to the rear end of said tub portion s that said fitting portion is disposed substantially on the exterior of said patient when said tip portion is in engagement with said inner stomach wall, said valve portion being threadedly received in said fitting portion and being disposed substantially in said fitting portion, said valve portion being operative for permitting the flow of a fluid into said tube portion from said fitting portion and for preventing the reverse flow of said fluid.

15. A gastrostomy feeding port comprising a tip portion, a tube portion, a fitting portion, and a valve portion, said tip portion being receivable through a preestablished stoma in the stomach of a patient and being operative for passing a fluid into said stomach, said tip portion including retaining means engageable with the inner wall of said stomach for preventing the inadvertent removal of said feeding port from said stoma, said tube portion communicating with said tip portion for passing said fluid thereto and extending rearwardly therefrom, said tube portion being dimensioned to extend outwardly through said stoma when said tip portion is in engagement with the inner wall of the stomach of said patient, said fitting portion being attached to the rear end of said tube portion so that said fitting portion is disposed substantially on the exterior of said patient when said tip portion is in engagement with said inner stomach wall, said valve portion being disposed substantially in said fitting portion and being operative for permitting the flow of a fluid into said tube portion from said fitting portion and for preventing the reverse flow of said fluid, said feeding port further comprising biasing means comprising an outwardly extending concave flange on said fitting portion facing toward said tip portion, said flange being resiliently deformable and being engageable with the skin of said patient adjacent said stoma for biasing said tip portion against the inner wall of the patient's stomach.

16. A gastrostomy feeding port comprising a tip portion, a tube portion, a fitting portion, and a valve portion, said tip portion being receivable through a preestablished stoma in the stomach of a patient and being operative for passing a fluid into said stomach, said tip portion including retaining means engageable with the inner wall of said stomach for preventing the inadvertent removal of said feeding port from said stoma, said tube portion communicating with said tip portion for passing said fluid thereto and extending rearwardly therefrom, said tube portion being dimensioned to extend outwardly through said stoma when said tip portion is in engagement with the inner wall of the stomach of said patient, said fitting portion being attached to the rear end of said tube portion so that said fitting portion is disposed substantially on the exterior of said patient when said tip portion is in engagement with said inner stomach wall, said valve portion being removably received in said fitting portion and being operative for permitting the flow of a fluid into said tube portion from said fitting portion and for preventing the reverse flow of said fluid, said feeding port further comprising biasing means comprising an outwardly extending concave flange on said fitting portion facing toward said tip portion, said flange being resiliently deformable and being engageable with the skin of said patient adjacent the stoma for biasing said tip portion against the inner wall of the patient's stomach.

* * * * *